United States Patent
Govari

(10) Patent No.: US 11,103,174 B2
(45) Date of Patent: Aug. 31, 2021

(54) REVERSE ECG MAPPING

(71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 33 days.

(21) Appl. No.: 14/528,967

(22) Filed: Oct. 30, 2014

(65) Prior Publication Data
US 2015/0133759 A1    May 14, 2015

Related U.S. Application Data

(60) Provisional application No. 61/903,484, filed on Nov. 13, 2013.

(51) Int. Cl.
*A61B 5/06*    (2006.01)
*A61B 5/316*    (2021.01)
(Continued)

(52) U.S. Cl.
CPC .............. *A61B 5/316* (2021.01); *A61B 5/282* (2021.01); *A61B 5/283* (2021.01); *A61B 5/287* (2021.01); *A61B 5/318* (2021.01); *A61B 5/6805* (2013.01); *A61B 5/6823* (2013.01); *A61B 5/6852* (2013.01); *A61B 5/7221* (2013.01); *A61B 5/7246* (2013.01); *A61B 5/0044* (2013.01);
(Continued)

(58) Field of Classification Search
CPC .......................... A61B 5/04085; A61B 5/6805
See application file for complete search history.

(56) References Cited

U.S. PATENT DOCUMENTS 5,054,496 A    10/1991  Wen et al.
6,494,832 B1 *  12/2002  Feldman ............. A61B 5/0422
                                                 600/301
(Continued)

FOREIGN PATENT DOCUMENTS

CN    101147676 A    3/2008
CN    201033076 Y    3/2008
(Continued)

OTHER PUBLICATIONS

Modre, Robert et al. Atrial Noninvasive Activation Mapping of Paced Rhythm Data. J Cardiovasc Electrophysiol, vol. 14, pp. 712-719, Jul. 2003.
(Continued)

*Primary Examiner* — Michael J D Abreu
(74) *Attorney, Agent, or Firm* — Louis J. Capezzuto

(57) ABSTRACT

Methods and systems for preparing electroanatomic maps of the heart operate using a probe that has been inserted into a heart chamber by emitting electrical calibration signals from external locations that are outside the subjects body, receiving the calibration signals in a plurality of intracardiac electrodes on the probe, and determining functional relationships between the emitted calibration signals and the received calibration signals. Thereafter, electrophysiological signals from respective origins in the heart are detected in the external locations, and the functional relationships are applied to the detected electrophysiological signals to calculate intracardiac potentials at the respective origins.

18 Claims, 2 Drawing Sheets

(51) Int. Cl.
*A61B 5/00* (2006.01)
*A61B 5/282* (2021.01)
*A61B 5/283* (2021.01)
*A61B 5/287* (2021.01)
*A61B 5/318* (2021.01)
*A61B 5/0538* (2021.01)

(52) U.S. Cl.
CPC ............ *A61B 5/0538* (2013.01); *A61B 5/061* (2013.01); *A61B 5/7207* (2013.01); *A61B 5/7289* (2013.01)

(56) References Cited

U.S. PATENT DOCUMENTS

| | | |
|---|---|---|
| 6,748,260 B2 * | 6/2004 | Au ................. A61B 5/0006 600/509 |
| 7,536,218 B2 | 5/2009 | Gavari |
| 7,599,730 B2 | 10/2009 | Hunter |
| 7,756,576 B2 | 7/2010 | Levin |
| 7,848,789 B2 | 12/2010 | Govari |
| 7,869,864 B2 | 1/2011 | Tseng |
| 7,869,865 B2 | 1/2011 | Govari et al. |
| 7,983,743 B2 | 7/2011 | Rudy et al. |
| 8,428,700 B2 | 4/2013 | Harlev |
| 8,456,182 B2 | 6/2013 | Bar-Tal |
| 2003/0083587 A1 * | 5/2003 | Ferek-Petric ...... A61B 5/04011 600/512 |
| 2003/0120163 A1 * | 6/2003 | Rudy ................. A61B 5/04085 600/509 |
| 2004/0039293 A1 * | 2/2004 | Porath ................. A61B 5/0422 600/509 |
| 2004/0068179 A1 | 4/2004 | Jutras |
| 2005/0182295 A1 | 8/2005 | Soper et al. |
| 2006/0173251 A1 | 8/2006 | Govari |
| 2007/0016007 A1 | 1/2007 | Govari |
| 2007/0038078 A1 | 2/2007 | Osadchy |
| 2007/0060832 A1 | 3/2007 | Levin |
| 2007/0106147 A1 * | 5/2007 | Altmann .................. A61B 8/12 600/407 |
| 2008/0058657 A1 | 3/2008 | Schwartz et al. |
| 2008/0214931 A1 | 9/2008 | Dickfeld |
| 2008/0294258 A1 | 11/2008 | Revie |
| 2009/0203992 A1 | 8/2009 | Govari et al. |
| 2009/0221907 A1 | 9/2009 | Bar-Tal |
| 2009/0297001 A1 | 12/2009 | Markowitz |
| 2010/0079158 A1 | 4/2010 | Bar-Tal |
| 2011/0238083 A1 | 9/2011 | Moll |
| 2013/0006137 A1 | 1/2013 | Hauck et al. |
| 2013/0085380 A1 | 4/2013 | Velusamy |

FOREIGN PATENT DOCUMENTS

| | | |
|---|---|---|
| CN | 201847775 U | 6/2011 |
| CN | 101199416 A | 6/2019 |
| EP | 1 005 677 B1 | 6/2000 |
| WO | 2012/174660 A1 | 12/2012 |

OTHER PUBLICATIONS

Ozawa, Yukio, M.D. New Approaches to the Analysis of ECG Data, Jpn J Clin Pathol 48:591-601, 2000.
U.S. Appl. No. 14/086,265, filed Nov. 13, 2013.
U.S. Appl. No. 61/903,494, filed Nov. 13, 2013.
Chinese Office Action dated Jul. 3, 2018.
Yesim Serinagaoglu et al: "Multielectrode venous catheter mapping as a high quality constraint for electrocardiographic inverse solution", Journal of Electrocardiology, vol. 35, No. 4, Oct. 1, 2002, pp. 55-73.
Martin V. et al. "MagnetoHemoKynamics in the Aorta and Electrocardiograms.", Physics in Medicine and Biology., Phys. Med. Bio. 57(2012)3177-3195.
CN201410641464.0—Notice of Reexamination dated May 29, 2019.
CN101147676—Translation and original application with drawings.
CN2010330767—Translation of abstract and drawings.
CN201847775U—Translation of abstract and drawings.

* cited by examiner

REVERSE ECG MAPPING

CROSS-REFERENCE TO RELATED APPLICATIONS

This Application claims the benefit of U.S. Provisional Application No. 61/903,484, filed Nov. 13, 2013, which is herein incorporated by reference.

BACKGROUND OF THE INVENTION

1. Field of the Invention

This invention relates to evaluation and treatment of cardiac arrhythmias. More particularly, this invention relates to improvements in electrical mapping of the heart for use in evaluation of cardiac arrhythmias and ablative therapy thereof.

2. Description of the Related Art

Methods are known for noninvasive mapping of electrical potentials in the heart based on body surface electrocardiographic (ECG) techniques. These methods combine 3-dimensional imaging with the ECG data in order to generate 3-dimensional maps of the electrical potentials on the epicardial surface, and on the endocardial surface, as well.

The document Modre et al., Atrial Noninvasive Activation Mapping of Paced Rhythm Data, J. Cardiovasc. Electrophysiology 14:712-719 (July 2003), describes a surface heart model activation time (AT) imaging approach, based on magnetic resonance imaging (MRI) and ECG mapping data. Both endocardial and epicardial surfaces might be mapped in this way. The AT pattern was compared to a CARTO™ map of atrial potentials. External anatomic markers were used to couple the CARTO data to the MRI coordinate system, by moving the catheter tip to marker locations at the body surface after internal mapping. It is proposed that AT imaging within the atria may be useful for noninvasive imaging of atrial activity in patients with focal arrhythmias.

U.S. Pat. No. 7,983,743 to Rudy et al., which is herein incorporated by reference, proposes noninvasive systems and methods for determining electrical activity for a heart of a living being. A processor is configured to meshlessly compute data that represents heart electrical activity from a set of noninvasively measured body surface electrical potentials. This is accomplished using data that describes a geometric relationship between a plurality of locations corresponding to where the body surface electrical potentials were measured and the heart.

Commonly assigned U.S. Patent Application Publication No. 2008/0058657 by Schwartz et al., which is herein incorporated by reference, describes construction of a matrix relationship between a small number of endocardial points and a large number of external receiving points using a multi-electrode chest panel. Inversion of the matrix yields information allowing the endocardial map to be constructed.

SUMMARY OF THE INVENTION

According to disclosed embodiments of the invention, weak stimulation signals are applied to skin patches and measure the signals received at a catheter in different locations in the heart to establish calibrate a functional relationship between the emitted and the received electrical signals. The relationship is reversible, so that the same calibration relations apply in reverse, allowing activity originating in the heart at different locations to be detected at the skin surface and mapped back to their sources in the heart. The stimulation signals used for calibration have no effect on cardiac electrical activity, and constitute no risk to the subject.

There is provided according to embodiments of the invention a method, which is carried out by inserting a probe into a chamber of a heart of a living subject, emitting electrical calibration signals from external locations that are outside a body of the subject, receiving the calibration signals in a plurality of intracardiac electrodes disposed in a distal portion of the probe the intracardiac electrodes, determining functional relationships between the emitted calibration signals and the received calibration signals. Thereafter, the method is further carried out by detecting electrophysiological signals at the external locations from respective origins in the heart, and applying the functional relationships to the detected electrophysiological signals to calculate intracardiac potentials at the respective origins.

One aspect of the method includes removing the probe from the subject prior to detecting electrophysiological signals at the external locations.

A further aspect of the method includes mapping the electrophysiological signals to the respective origins.

According to yet another aspect of the method, the external locations comprise a plurality of skin electrodes disposed within a torso vest, the skin electrodes being in galvanic contact with a skin surface of the subject.

According to still another aspect of the method, there are between 125 and 250 skin electrodes.

According to an additional aspect of the method, receiving the calibration signals includes filtering the calibration signals to exclude potentials that are generated from electrical activity of the heart.

According to another aspect of the method, determining functional relationships includes expressing the functional relationships as a matrix has elements, wherein values of the elements depend on respective distances and conductivities between the external locations and the intracardiac electrodes.

According to one aspect of the method, applying the functional relationships to the detected electrophysiological signals includes inverting the matrix.

Yet another aspect of the method includes gating the electrical calibration signals only during phases of a cardiac cycle of the subject, wherein expressing the functional relationships as a matrix includes constructing a plurality of gated matrices for respective ones of the phases of the cardiac cycle.

According to a further aspect of the method, gating the electrical calibration signals includes generating the electrical calibration signals only during phases of a respiratory cycle of the subject.

There is further provided according to embodiments of the invention an apparatus for carrying out the method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

Figure 1:
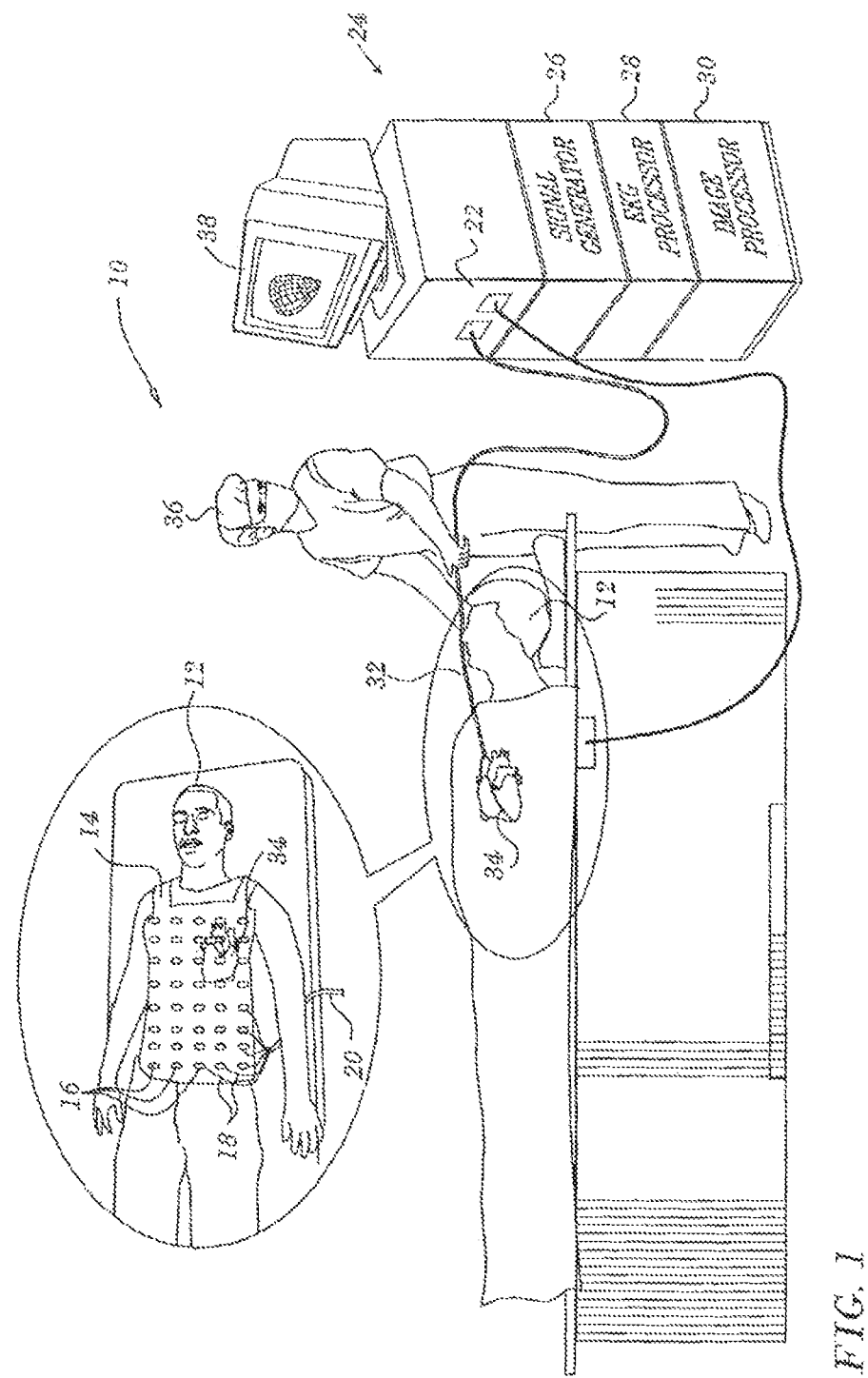
FIG. 1 is a pictorial illustration of a system, which is constructed and operative in accordance with an embodiment of the invention.

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a USB memory, hard drive, electronic media or CD-ROM. The code may be distributed on such media, or may be distributed to users from the memory or storage of one computer system over a network of some type to storage devices on other computer systems for use by users of such other systems.

A conventional method for mapping electropotentials of the heart, i.e., measuring intra-cardiac ECG signals, involves inserting a catheter with electrodes into the heart, and measuring potentials as the electrodes are moved to different locations within the heart.

Reverse ECG mapping, an example of which is described in U.S. Pat. No. 7,983,743, cited above, attempts to generate an intra-cardiac ECG map by measuring body surface potentials at an array of positions on the skin of a patient. The method assumes that intra-cardiac ECG potentials $\vec{E}$ generate body surface potentials $\vec{S}$ S and that the two sets of potentials are related by an equation of the form:

$$\vec{S} = M \cdot \vec{E} \quad (1),$$

where M is a matrix, having elements $m_{ij}$.

The values of elements of the matrix M depend, inter alia, on the distance between the positions on the heart surface and the positions on the patient's skin, and on the conductivity of the material between these positions. The '743 Patent uses a non-invasive approach to estimate the matrix M (using systems such as MRI or CT to image the heart and thus find heart surface–skin distances). According to the '743 Patent vector $\vec{E}$ is then estimated from measured values of the vector $\vec{S}$.

In contrast, embodiments of the present invention take an invasive approach to determine the matrix M. In an initial phase of a mapping procedure for a patient an electrode array, with electrodes in known positions, is attached to the patient's skin. Assuming the procedure is being performed, a system having location tracking capabilities is used. For example, the positions of the electrodes in the array and the electrodes of a cardiac catheter can be determined by the CARTO® 3 System, available from Biosense Webster, Inc., 3333 Diamond Canyon Road, Diamond Bar, Calif. 91765. Any other method for finding electrode position may be used.

Reference is now made to FIG. 1, which is a pictorial illustration of a system 10, which is constructed and operative in accordance with an embodiment of the invention. A subject 12 is clothed in a torso vest 14. A plurality of electrodes 16, typically between about 125 and 250 electrodes, are disposed within the torso vest 14 in galvanic contact with the skin of the subject 12, and can transmit and receive electrical potentials over the anterior, posterior and lateral aspects of the torso of the subject 12. The electrodes 16 are connected via leads 18 and cable 20 to a control processor 22, which is typically disposed in a console 24. The console 24 may include a signal generator 26, an EKG processor 28 and an image processor 30.

A catheter 32 has been introduced into a heart 34 by an operator 36. Information relating to the data obtained from the catheter 32, the status of the electrodes 16 of the torso vest 14 and the signal generator 26, EKG processor 28 and image processor 30 may be displayed on a monitor 38.

U.S. Pat. No. 7,869,865 to Govari, which is assigned to the assignee of the present patent application and whose disclosure is incorporated herein by reference discloses an embodiment of the control processor 22 that contains electrical circuitry for which can be used for impedance detection, as described in U.S. Patent Application Publication No. 2007/0106147 and commonly assigned copending application Ser. No. 14/086,265, both of which are herein incorporated by reference. The system generates, based on impedance measurements between a small number of endocardial points and the electrodes 16, a multidimensional matrix of coefficients, referred to herein as a lead field matrix. The inverse of the matrix is then estimated, for example, as described in U.S. Patent Application Publication No. 2003/0120163 by Yoram Rudy et al., whose disclosure is herein incorporated by reference. In the Rudy et al. disclosure, the inverse matrix corresponds to epicardial electrical potentials. In the system 10, however, the inverse of the matrix corresponds to a map of endocardial conductances. Practical techniques and optimizations for the inversion of the lead field matrix are known from the above-referenced U.S. Patent Application Publication No. 2008/0058657.

As will be seen from the discussion below, according to embodiments of the invention, in a calibration operation for the system 10, the electrodes 16 of the torso vest 14 may inject known source signals into the body of the subject 12. The signals are detected by electrodes of the catheter 32, which is located within the heart. The control processor 22 is programmed to cooperate with the signal generator 26 for selection of the electrodes 16, for configuration and transmission of the injected signals, and for receiving and processing data from receiving elements within the subject 12 to establish the elements of the matrix M.

Figure 2:
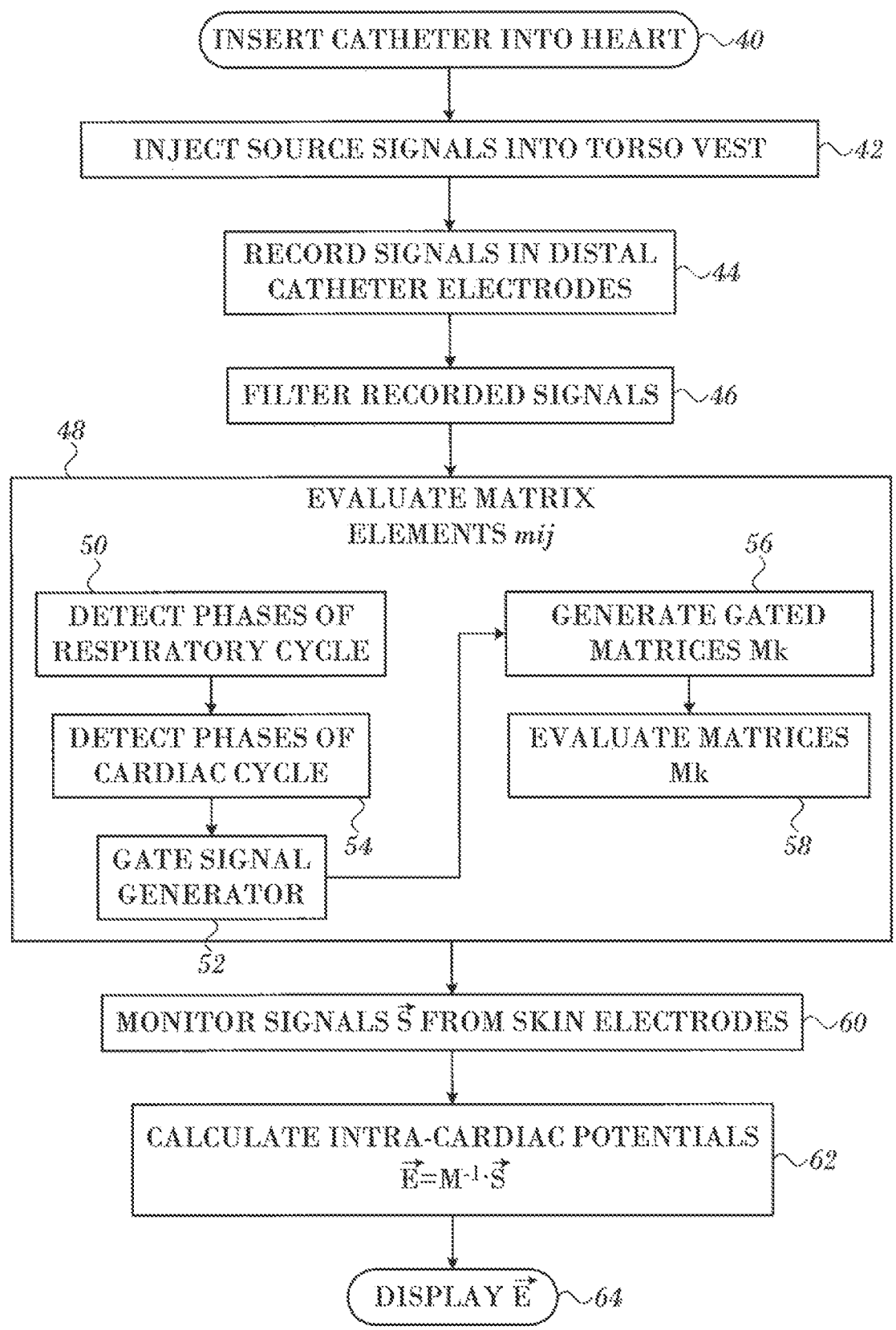
FIG. 2 is a flow-chart of a procedure for calibration and operation of the instrumentation used in reverse ECG mapping, in accordance with an embodiment of the invention.

Reference is now made to FIG. 2, which is a flow-chart of a procedure for calibration and operation of the instrumentation used in reverse ECG mapping, in accordance with an embodiment of the invention. The process steps are shown in a particular linear sequence in FIG. 2 and other drawing figures herein for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 40 A catheter having an electrode is inserted into the patient's heart, and the position of the electrode is tracked by the processor. While the catheter is in the heart, at step 42 the processor injects respective known source signals that do not affect the patient's heart or interfere with the generated ECG potentials, into the electrodes 16 of the torso vest 14. For example, an injected source signal may have an amplitude of 2 mV and a frequency of 300 Hz. The injection is repeated at multiple known electrode positions within the heart. Using filtering or multiplexing, multiple signals at different frequencies can be injected into more than one of the electrodes 16.

During the signal injection, at step 44 the system processor records the signals picked up by electrodes in the distal portion of the catheter 32. At step 46 the raw signals at the catheter electrodes include are filtered to exclude potentials that are generated from the electrical activity of the heart using the known characteristics of the injected signal. Appropriate filters are provided in the above-referenced CARTO system. At the conclusion of the calibration phase, at step 48 the processor uses the recorded signals, together with the known positions of the electrodes injecting and receiving the signals to evaluate elements of M, $\{m_{ij}\}$. Step 48 comprises the following steps.

The elements $m_{ij}$ of the elements of the matrix M vary with the cardiac and respiratory cycles, as the distances between the electrodes 16 and the catheter electrodes vary. While these could be ignored by providing average values for the elements $m_{ij}$, it is preferable to provide reliable calibration information at all phases of the physiologic cycles at a desired resolution by collecting the signals over time. Step 50 provides one way of accomplishing this: the phase of the respiratory cycle is detected by known methods, e.g., measurement of intrathoracic pressures or pressure-volume relationships. In step 52 these relationships, together with information obtained from the EKG processor 28 in step 54 may be used by the control processor 22 to gate the signal generator 26. An array of gated matrices $M_k$ is generated, and then evaluated to determine their respective elements $m_{ij}$. For each of the matrices, at the conclusion of the calibration phase, the control processor 22 uses the recorded signals from the catheter electrodes, together with the known positions of the electrodes 16 that injected the signals (and thus the distances to the catheter electrodes) to generate the elements $m_{ij}$ of each the matrices $M_k$ in step 56 and evaluate the matrices $M_k$ in step 58.

Optionally, gated arrays of matrices $M_k$ may be generated at different locations within the heart, either by employing catheters having multiple mapping electrodes, or by navigating the catheters to positions relative to known landmarks.

Subsequently, in an operational phase of the procedure, (during which phase the catheter may or may not be present) in step 60 the processor monitors signals $\vec{S}$ registered by the skin electrodes. Then in step 62 The processor then uses selected matrices $M_k$ as the matrix M by rearranging equation (1) to calculate intra-cardiac potentials $\vec{E}$ at different phases of the cardiorespiratory cycles:

$$\vec{E} = M^{-1} \cdot \vec{S} \qquad (2).$$

Typically, as shown in the figure, in final step 64 the processor displays potentials $\vec{E}$ on a map of the heart, although other types of display, such as potential-time graphs, may also be used.

Equation (1) assumes a generally linear relationship between a given element of $\vec{S}$ and the elements of $\vec{E}$, with matrix elements $m_{ij}$ as coefficients of $\vec{E}$. There is a similar relationship for equation (2). For example, patient breathing and the heart beating change the distances involved, which change the values of the elements $m_{ij}$ as noted above.

Conventional invasive mapping procedures, using one or more catheters with multiple electrodes, can only provide electropotential mapping while the catheters are in the heart, and the mapping is only valid at the positions of the electrodes. In contrast, once the matrix M is obtained by reverse ECG mapping, such as is described herein, an accurate electroanatomic mapping is obtained. Indeed, the procedure can provide real-time patient-specific electropotential mapping over the whole heart surface, without the necessity of a catheter being in the heart. Additionally or alternatively, the mapping procedure described herein may be performed together with another invasive procedure, such as ablation.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:
1. A method, comprising:
a calibration phase and an operation phase;
the calibration phase comprising the steps of:
inserting a probe into a position in a chamber of a heart of a living subject, a plurality of intracardiac electrodes being disposed in a distal portion of the probe;
emitting electrical calibration signals having known amplitude and frequency characteristics from a first plurality of skin electrodes located at a plurality of external locations that are located on the skin of the subject;
receiving the electrical calibration signals in the intracardiac electrodes located at the position;
filtering the received electrical calibration signals to exclude potentials that are generated from the electrical activity of the heart using the known amplitude and frequency characteristics of the electrical calibration signals;
determining functional relationships between the emitted electrical calibration signals, the filtered received electrical calibration signals in the intracardiac electrodes;
the operation phase comprising the steps of:
detecting electrophysiological signals by a second plurality of skin electrodes located at the plurality of external locations, the electrophysiological signals originating from respective origins in the heart; and
applying the functional relationships to the detected electrophysiological signals to calculate intracardiac potentials at the respective origins;
wherein determining functional relationships comprises expressing the functional relationships as a matrix having elements, values of the elements depending on respective distances and conductivities between the first plurality of skin electrodes and the intracardiac electrodes based on the position of the probe in the chamber of the heart of the plurality of external location of the first plurality of skin electrodes.

2. The method according to claim 1, wherein the first and second plurality of skin electrodes are disposed within a torso vest, the skin electrodes being in galvanic contact with a skin surface of the subject.

3. The method according to claim 2, wherein each one of the first and second plurality of skin electrodes comprise between 125 and 250 skin electrodes.

4. The method according to claim 1 further comprising gating the electrical calibration signals only during phases of a cardiac cycle of the subject, wherein expressing the functional relationships as a matrix comprises a constructing a plurality of gated matrices for respective ones of the phases of the cardiac cycle.

5. The method according to claim 4, wherein gating the electrical calibration signals further comprises generating the electrical calibration signals only during phases of a respiratory cycle of the subject.

6. The method according to claim 1, further comprising removing the probe from the subject prior to detecting electrophysiological signals at the external locations.

7. The method according to claim 1, further comprising mapping the electrophysiological signals to the respective origins.

8. The method according to claim 1, wherein receiving the calibration signals comprises filtering the calibration signals to exclude potentials that are generated from electrical activity of the heart.

9. The method according to claim 1, wherein applying the functional relationships comprises inverting the matrix.

10. An apparatus, comprising:
  a probe adapted for insertion into a chamber of a heart of a living subject, a plurality of intracardiac electrodes being disposed in a distal portion of the probe;
  a signal generator for emitting electrical calibration signals having known amplitude and frequency characteristics from a plurality of skin electrodes located at a plurality of external locations that are located on the skin of the subject;
  first electrical circuitry connected to the intracardiac electrodes for receiving the electrical calibration signals;
  a processor linked to the first electrical circuitry, the processor operative during a calibration phase for:
    determining a position of the probe in the chamber of the heart;
    filtering the electrical calibration signals to exclude potentials that are generated from the electrical activity of the heart using the known amplitude and frequency characteristics of the electrical calibration signals and
    determining functional relationships between the emitted electrical calibration signals and the filtered received electrical calibration signals; and
  second electrical circuitry for detecting electrophysiological signals by a plurality of skin electrodes located at the plurality of external locations, the electrophysiological signals originating from respective origins in the heart;
  wherein the processor is linked to the second electrical circuitry and is operative during an operational phase for applying the functional relationships to the detected electrophysiological signals to calculate intracardiac potentials at the respective origins; and
  wherein determining functional relationships comprises expressing the functional relationships as a matrix having elements, values of the elements depending on respective distances and conductivities between the first plurality of skin electrodes and the intracardiac electrodes based on the position of the probe in the chamber of the heart of the plurality of external location of the first plurality of skin electrodes.

11. The apparatus according to claim 10, further comprising a torso vest, wherein the first and second skin electrodes are the same skin electrodes and are disposed on the torso vest, the torso vest adapted to place the skin electrodes in galvanic contact with a skin surface of the subject.

12. The apparatus according to claim 11, wherein the skin electrodes comprise between 125 and 250 skin electrodes.

13. The apparatus according to claim 10 further comprising gating circuitry for gating the electrical calibration signals only during phases of a cardiac cycle of the subject, wherein expressing the functional relationships as a matrix comprises a constructing a plurality of gated matrices for respective ones of the phases of the cardiac cycle.

14. The apparatus according to claim 13, wherein gating the electrical calibration signals further comprises generating the electrical calibration signals only during phases of a respiratory cycle of the subject.

15. The apparatus according to claim 10, further comprising a display, wherein the processor is operative for mapping the electrophysiological signals to the respective origins on the display.

16. The apparatus according to claim 10, wherein applying the functional relationships comprises inverting the matrix.

17. The method of claim 10, wherein the first and second plurality of skin electrodes comprise the same electrodes.

18. The apparatus of claim 10, wherein the first and second plurality of skin electrodes comprise the same electrodes.

* * * * *